United States Patent [19]
Tiemann et al.

[11] Patent Number: 5,057,079
[45] Date of Patent: Oct. 15, 1991

[54] SHEATHING DEVICE FOR AFTER USE PROTECTION FROM A SYRINGE NEEDLE

[76] Inventors: Roland Tiemann; Kevin Churchill, both of 2681 Ponderosa Rd., Shingle Springs, Calif. 95682

[21] Appl. No.: 523,706
[22] Filed: Apr. 3, 1990
[51] Int. Cl.⁵ .............................................. A61M 5/00
[52] U.S. Cl. .................................... 604/110; 604/198; 604/263
[58] Field of Search ............... 604/110, 198, 263, 187, 604/192, 197

[56] References Cited
U.S. PATENT DOCUMENTS 3,890,971 6/1975 Leeson et al. .
4,631,057 12/1986 Mitchell .
4,747,837 5/1988 Hauck .
4,752,290 6/1988 Schramm .
4,790,827 12/1988 Haber et al. .
4,826,491 5/1989 Schramm .
4,832,696 5/1989 Luther et al. .
4,931,048 6/1990 Lopez ................... 604/110
4,961,730 10/1990 Poncy ..................... 604/198

FOREIGN PATENT DOCUMENTS

96637 8/1960 Norway .
1191634 5/1970 United Kingdom .
2209946 6/1989 United Kingdom .

Primary Examiner—John D. Yasko
Attorney, Agent, or Firm—James M. Ritchey

[57] ABSTRACT

A syringe sheathing device is provided that shields a user from post-use needles that are still attached to a syringe. A cylindrical protective sheath fits over the syringe and may be extended irreversibly from a pre-use to a post-use position covering a used needle by sliding or telescoping the sheath past an easily dislodged pre-use position into the locked configuration. The pre-use configuration is easily assembled for delivery to a consumer.

17 Claims, 5 Drawing Sheets

SHEATHING DEVICE FOR AFTER USE PROTECTION FROM A SYRINGE NEEDLE

BACKGROUND OF THE INVENTION

1. Field of the Invention

The field of the invention is safety syringe needle covers or sheaths. Due to the possible presence of various infectious agents, there are grave dangers associated with unprotected post-use syringe needles. The subject device lowers the probability of these infectious agents being transmitted to a post-use handler of the needle mounted syringe via a needle prick by permitting the user to immediately cover the needle with a locking cover or sheath.

2. Description of the Background Art

Traditionally, devices that have been designed to protect users and others from syringe mounted needles have focused on protecting either the free, unattached needle or when the needle is associated with a syringe. However, when the device is incorporated into the outer barrel of a syringe, the protection device is very complex, costly to produce, subject to accidental complete removal by applying too much force in extending the protective cover, or not easily assembled by the manufacturer for production and shipment to consumers.

Disclosed in the patent from Norway, No. 96637, is a typical needle cover that latches directly onto the surrounding support of the needle and not the syringe. The cover is held in place by a simple pressure fit between mated teeth. To employ the cover the user must insert the needle tip into a relatively small cover opening without pricking themselves during the motion where the needle tip approaches their hand.

The patent from Great Britain, No. 1,191,634, relates a pair of covers that protect a double-pointed-ended needle intended for use with a tubular-vial syringe. Bayonet mounts are placed proximate both ends of a double-pointed-ended needle. Appropriately mated bayonet mount covers fit over the needle ends for protection.

U.S. Pat. No. 3,890,971 discloses a safety syringe for one time use. A sheath slides between inner and outer cylinders and is held in an extended, safety locked position by mating indents on the sheath with detents on the inner and outer cylinders. Further, the plunger is lockable after delivering a plunger piston to the bottom of an ampul that is fitted with the syringe and carries the injectable solution.

A shielded needle mounted to a syringe is described in U.S. Pat. No. 4,631,057. A cylindrical guard having on the interior a conical cam surface and bearing teeth at one end and an annular rib at the other. The syringe barrel has a collar proximate its needle that receives the upper ledge of the cam surface under a shoulder of the collar when the guard is extended. The teeth aid in preventing the guard from coming completely off the syringe by catching an annular groove that normally functions to hold the guard in the non-extended position by mating with the annular rib of the guard.

Disclosed in U.S. Pat. Nos. 4,752,290 and 4,826,491, both to Schrann for slightly modified inventions, is a needle bearing medical device with a three-position shield. The device presents a shield that may be positioned in fully extended, fully retracted, and an intermediate location about the syringe. A protective cap fits over the end of the shield and must be removed before use. Either an annular rib or downwardly disposed teeth, or a tooth, on the syringe mate with upwardly disposed teeth on the shield to secure the positions. A cut-out in the shield permits the required longitudinal movement.

U.S. Pat. No. 4,747,837 relates a syringe needle recapping protective device. An annular flange or multiple teeth secured to the inner lining of the sleeve lock the sleeve over a needle by being lodged between two annular locking ribs or teeth located of the barrel of the syringe proximate the needle.

A shielded safety syringe is depicted in U.S. Pat. No. 4,790,827. Various axially locking designs are presented for securing a protection sleeve over a needle attached to a syringe tip. An extendable and retractable sleeve has means for being secured in covered and protected positions. An inwardly projecting means from the sleeve, rides over and drops behind a stop member to anchor the sleeve in either the extended or retracted positions.

A protective device directly associated with a syringe needle is disclosed in U.S. Pat. No. 4,823,696. A protective guard telescopes over the needle after use. The protective guard is secured to needle itself and not directly to the syringe.

British Patent No. 2,209,946 relates a needle safety device. The device is a concentric series of interlocking cylinders that attach proximate the needle attachment point on a syringe and telescope over the needle. The protective cylinders are not associated with the outer portion of the syringe barrel.

SUMMARY OF THE INVENTION

An object of the present invention is to produce a safety cover for a syringe that may be easily and irreversibly extended from a pre-use to a post-use configuration.

Another object of the present invention is to provide a syringe safety cover that may be easily and irreversibly assembled for shipping to a consumer in a pre-use form.

An additional object of the present invention is to furnish a shield that has few parts and is inexpensive to produce, yet reliably irreversible in its locking over a used needle.

A further object of the present invention is to produce a retrofit device that will permit a consumer to adapt a non-safety syringe into a fully protectable version that permits the user to sheath the post-use needle.

The subject invention, a sheathing device for after or post-use protection from a possibly contaminated needle, comprises a generally cylindrical sheath that covers a syringe body and needle. The generally cylindrical syringe body has an outer surface and an inner surface. An inner surface surrounds a body longitudinal central cavity entering the body at a proximal end and exiting the body at a restricted needle mounting distal end.

The cylindrical sheath comprises an outer surface and an inner surface with the inner surface surrounding a longitudinal central bore running between the proximal and distal sheath ends. For receiving and encircling the syringe body, the sheath central bore has a diameter matched to fit around the syringe body.

A first locking means is associated with the syringe body for locking the sheath around the body in a pre-use, retracted position. This first locking means includes an annular stopping channel with proximal and distal walls that has at least one locking ramp projecting from the proximal wall toward the body distal end. This locking ramp substantially narrows the stopping channel at the point of closest approach by the ramp to the distal wall.

Second locking means are associated with the syringe body for locking the sheath in an extended position that covers both a portion of the body proximate the distal end and all of the needle in a protective post-use position. Included in the second means is at least one annular element protruding above the outer body surface and at least one stop element protruding above both the outer body surface and the annular element and displaced from the annular element toward the distal body end.

Additionally, the sheath has a dual role locking means. This sheath locking means is associated with the sheath proximal end and protrudes inwardly for locking the sheath in both pre-use and post-use positions.

For the syringe retrofit version of this safety device, the locking components previously associated with the syringe body are now attached to a collar that fits over and adheres to the syringe body. To secure the collar to the syringe, means are provided that usually comprise an adhesive strip for contacting both the syringe surface and the collar surface.

Other objects, advantages, and novel features of the present invention will become apparent from the detailed description that follows, when considered in conjunction with the associated drawings.

DESCRIPTION OF THE PREFERRED EMBODIMENT

Referring now to FIGS. 1-5, there is shown a preferred embodiment of a safety sheathing device 4 for a syringe and a retrofit embodiment for a syringe. Once a needle fitted syringe is used for an injection or withdrawal the needle is a hazard that may transmit dangerous particles.

Figure 1:
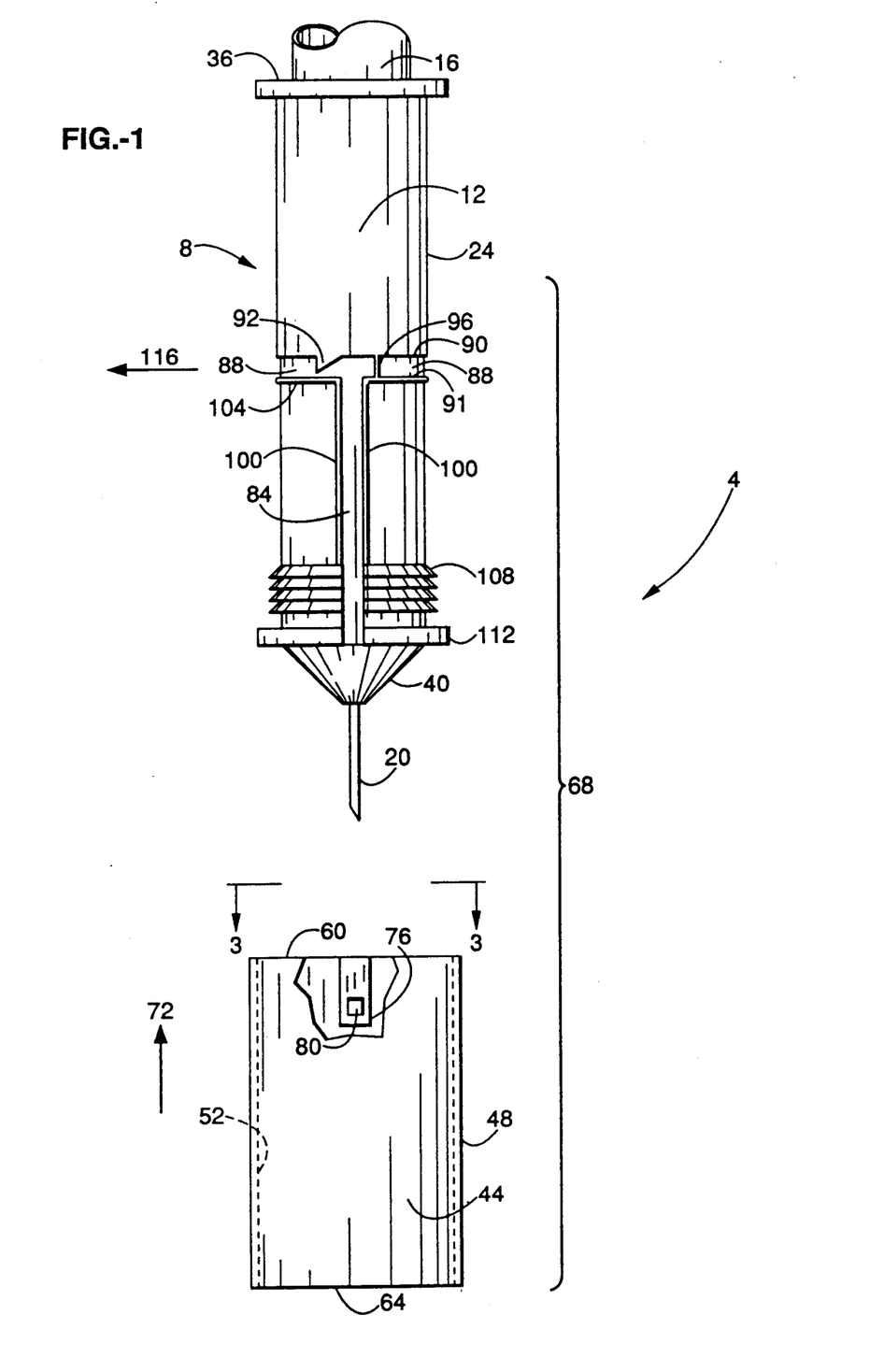
FIG. 1 is a side view of the subject device showing the separated syringe body and the sheath before the sheath is placed over the body and locked into pre-use configuration.
Figure 2A:
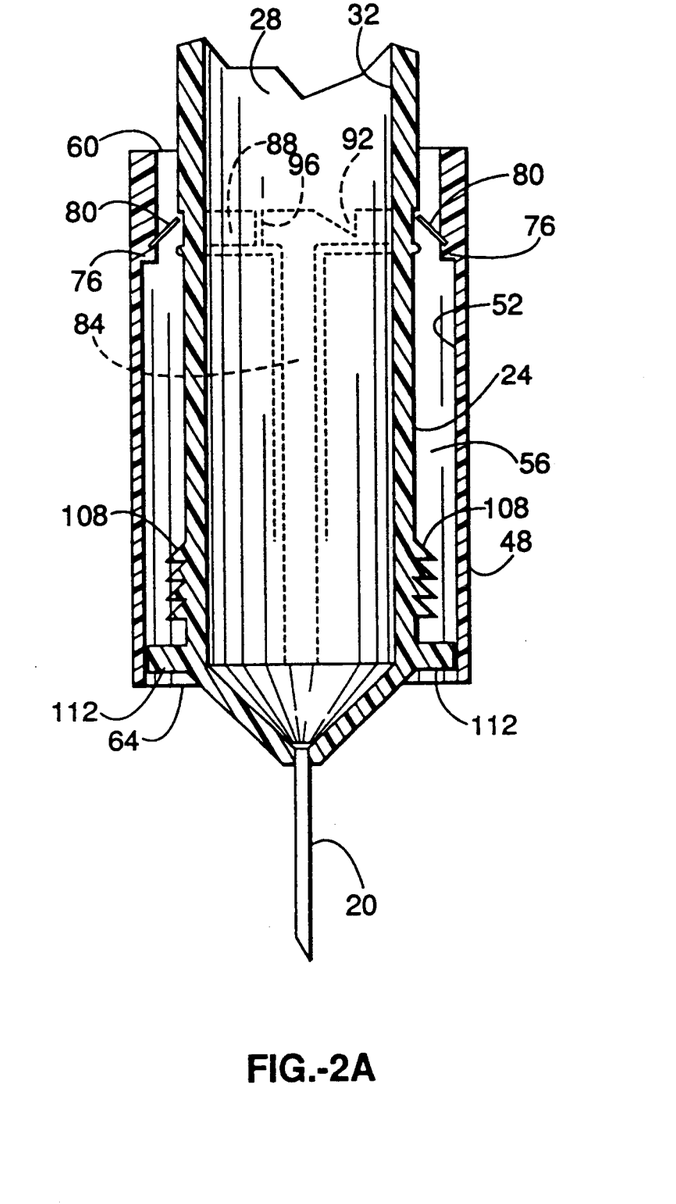
FIG. 2a is a cross-sectional side view of the subject device with the sheath in the pre-use retracted position.
Figure 2B:
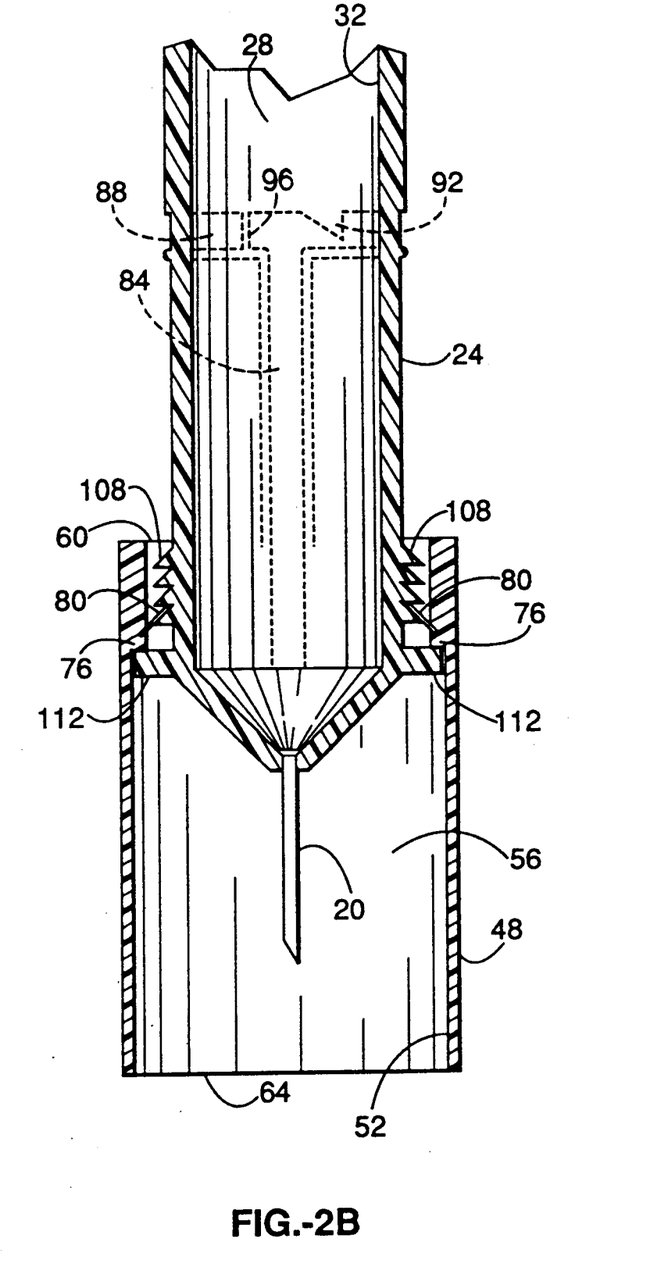
FIG. 2b is a cross-sectional side view of the subject device with the sheath in the post-use extended position.
Figure 3:
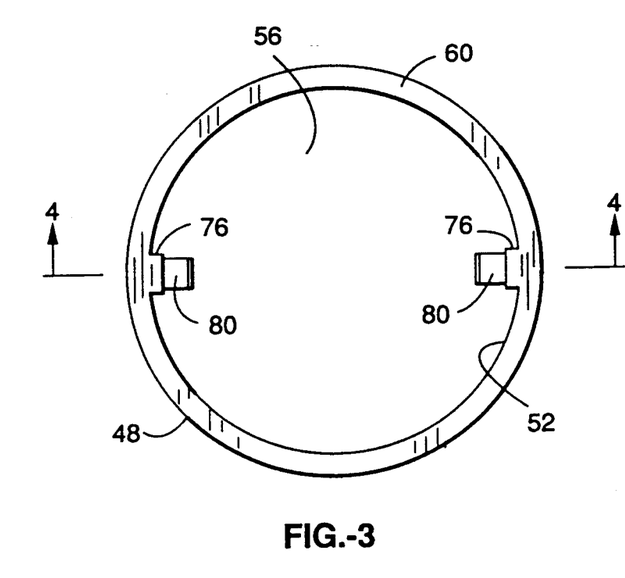
FIG. 3 is a top view of the subject device sheath.
Figure 4:
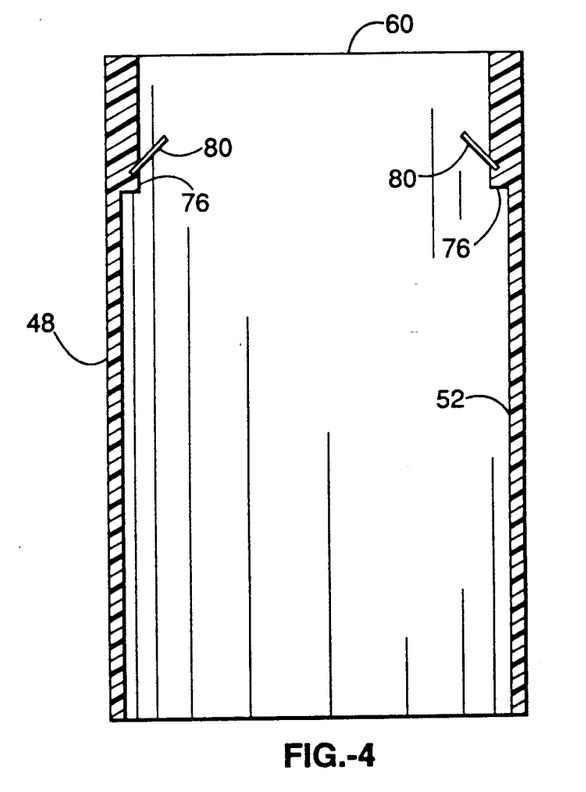
FIG. 4 is a cross-sectional side view of the subject device sheath taken along line 4—4 of FIG. 3.

FIG. 1 shows the subject device 4 in an unassembled form. Although it must be remembered that syringes differ in style, a general construction for a syringe 8 comprises a cylindrical syringe body 12, a plunger 16, and a needle 20. Variations from this configuration may easily be extended to the subject device. The syringe body 12 has an outer surface 24 that is usually substantially smooth of marked with graduations to indicate containing volumes. Longitudinally penetrating the syringe body 12 is a central cavity 28 (see, FIG. 2 for an assembled cross-sectional view of the subject device) surrounded by the syringe body inner surface 32. The longitudinal central cavity 28 enters the body 12 at a proximal syringe body end 36 and exits at a restricted needle mounting distal end 40. The depicted syringe in FIGS. 1 and 2 has a permanently mounted needle 20 such as would be employed on a typical disposable syringe. However, the subject device is equally suitable for use with a syringe that exploits a detachable needle.

A cylindrical protective sheath 44 has generally concentric outer 48 and an inner 52 surfaces. The inner surface 52 surrounds the sheath longitudinal central bore 56 that runs between a proximal sheath end 60 and a distal sheath end 64. The diameter of the sheath central bore 56 is selected to be sufficiently wide to receive and encircle the syringe body 12, but not excessively wide to permit inordinate sideways movement during the telescoping longitudinal protective deployment of the sheath 44 sliding over the body 12 (the details of this movement are presented below). The non-assembled but aligned for assembly (sheath 44 aligns with a common longitudinal axis to the syringe body 12) subject device is indicated in FIG. 1 by the bracket 68. The sheath 44 is moved toward and eventually around the syringe body 12 along the direction indicated by arrow 72. Preferably, before shipping the subject device to a consumer, it is assembled with the sheath 44 over the syringe body 12. As will be indicated below, an extremely easy assembly process is a beneficial result of the subject device.

Preferably, the sheath 44 is constructed from a polymer material such as plastic or rubber, but may be of any suitable substance including metal, paper, and wood materials. The sheath 44 is usually an extruded or poured object, but may be produced by any suitable means such as milling, cutting and forming, and like procedures.

Three separate locking areas are affiliated with the subject invention, two with the syringe body 12 and one with the sheath 44. Associated with the sheath proximal end 60 is a locking means comprising a small radial section ledge stop 76 that protrudes inwardly or is inset into the sheath central bore 56 from the sheath's inner surface 52. A sheath has at least one of these ledge stops 76, preferably two, but any number is contemplated to be within the realm of this disclosure. Secured proximate the ledge stop 76 and projecting at an inward angle towards the sheath proximal end 60 is a flexible locking pawl 80. This pawl 80 is usually flattened, but may be of other functionally equivalent shape and is flexible only in the direction of away from or into the inner sheath surface 52 proximate where the attachment is located. The pawl 80 is attached either directly to the ledge stop 76 or immediately adjacent and below the pawl 80 toward the sheath distal end 64. This attachment is by standard techniques such as imbedding, gluing, heating, and the like. As will be fully described below, the flexible pawl 80 cooperates with either of the other two body locking areas to secure the sheath 44 in the retracted or extended forms. The pawl 80 is fabricated from various flexible material such as thin metal or plastic and may be an integral extension of the sheath 44 material.

Associated with the body 12 is a first locking means that holds the sheath 44 in a pre-use or retracted position where the sheath 44 surrounds the syringe body 12, but the needle 20 is not protected by the sheath 44. This pre-use configuration would be the preferred assembly for shipping to a consumer. (In the retracted configuration, the exposed needle 20 would have a sterile temporary cover or cap that would be removed before use.) At the distal end 40 of the syringe body 12 is at least one, preferably two, or more longitudinal receiving channels 84. The receiving channel 84 has first and second ends wherein the first end is proximate the body distal end 40. Interior wall surfaces line the receiving channel 84. A cross-section of the receiving channel 84 shows a generally square or rectangular form, but other equivalent structures are anticipated. The receiving channel 84 is formed into the syringe body outer surface 24. Each receiving channel 84 has a depth suitable for receiving a sheath ledge stop 76 and associated flexible locking pawl 80 within it as a sheath 44 is slid around a syringe body 12 having such a receiving channel 84.

A first locking means associated with the syringe body 12 comprises an annular stopping channel 88, a locking ramp 92, and a channel block 96. At the second end of the longitudinal receiving channel 84 is at least one annular stopping channel 88. Each stopping channel 88 has a proximal 90 and distal 91 wall, with the distal wall 91 closest the syringe distal end 40. Within each stopping channel 88 is at least one locking ramp 92 that continues and projects away from the proximal wall 90 into the annular stopping channel 88. The ramp 92 substantially narrows the stopping channel 88 at the point where the tip on the ramp 92 approaches the distal wall 91. Also with the annular stopping channel 88 is at least one channel block 96. The channel block 96 completely cuts off and blocks the annular stopping channel. As seen in FIG. 1, each longitudinal receiving channel 84 intersects an annular stopping channel 88 at the receiving channel's 84 second end. Generally, to one side of this intersection, and within the annular stopping channel 88, is a locking ramp 92 and to the other side is a channel block 96.

Extending approximately the length of each longitudinal receiving channel 84 wall outer edge and protruding slightly above the syringe body surface 24 is a longitudinal channel edge lip 100. Further, an equivalent annular stopping channel edge lip 104 extends along the edge length of the annular stopping channel distal wall 91 and protrudes slightly above the syringe body surface 24.

A second locking means is associated with the syringe body 12. This second locking means is for locking the protective sheath 44 in the post-use or extended configuration and comprises at least one annular element protruding above the outer body surface 24 and at least one stop element protruding above both the outer body surface 24 and the annular element. The extended, post-use position has the sheath 44 covering both a portion of the body 12, surrounding the syringe distal end 40, and all of the needle 20. Preferably, the annular element is a locking tooth 108. The locking tooth 108, or a plurality of such, angle toward the body distal end 40 and positioned proximate the body distal end 40. Each annular locking tooth 108 nearly encircles the syringe body 12 and is broken only by the longitudinal receiving channel 84 with its associated edge lips 100. It should be noted that each lip 100 protrudes not only slightly beyond the outer body surface 24, but slightly past each locking tooth 108. Clearly, more than one such locking tooth 108 may be employed to generate a series of teeth.

Distal to the annular locking element or annular stop 112. As indicated, this annular stop 112 protrudes outwardly from the body surface 24 past the furthest extent of the annular tooth 108. Like the annular locking tooth 108, the annular stop is broken only by the longitudinal receiving channel 84. The diameter of the outer perimeter edge of the annular stop 112, taken through the center of the syringe body 12, is sufficiently less than the diameter of the sheath central bore 56 to permit the stop fitted syringe 8 to slide readily within the sheath 44.

A detailed description of the assembly procedure to generate the pre-use or retracted assemblage of a sheath 44 and a syringe body 12 and the extension of the sheath 44 into the post-use or extended assemblage is now possible. As seen in FIG. 1, the sheath 44 is aligned with a common longitudinal axis to the syringe body 12. To allow the sheath 44 to mate with the syringe body 12, the sheath ledge stop 76 and associated locking pawl 80 are aligned with a longitudinal receiving channel 84. Each sheath ledge stop 76 and pawl 80 are inserted within a receiving channel 84 and the sheath 44 is slipped over the syringe body 12 in the direction indicated by movement arrow 72. The sheath 44 is slid up the syringe body 12 until the inwardly projecting pawl 80 contacts the proximal wall 90 of the annular stopping channel 88, thereby preventing further movement of the sheath 44 toward the syringe proximal end 36. The sheath 44 is the rotated in the direction of the rotational movement arrow 116. (The direction of rotation may be in either direction, but the orientation of the ramp 92 and channel block 96 would need to be reversed from that shown in the drawings.) The locking pawl 80 rides over the ramp 92 and slip through the narrowed opening in the annular channel 88 and behind the ramp 92. These movements generate the pre-use configuration for the subject device. The pawl 80 holds the sheath 44 in a retracted position by being force within the annular stopping channel 88 (see, FIG. 2a). The ramp 92 and the block 96 cooperate to prevent the pawl 80 from rotating out of the annular stopping channel 88 and back into the longitudinal receiving channel 84. This simple process permits the easy assemble of the device by the manufacturer into the retracted configuration. Many of the referenced devices require considerable force to achieve their initial retracted structure or must be assembled by complex routes into the retracted form.

To deploy the sheath 44 over the needle 20 for protection post-use, the sheath 44 is extended merely by sliding it from the retracted position down the syringe body 12 (see, FIG. 2b for a cross-sectional view of the extended form). This downward motion forces the pawl 80 from the annular stopping channel 88, causing it to ride over the annular channel distal wall 91 and annular channel edge lip 104. As the compressed pawl 80 slides along the syringe body 12 it can not re-enter the receiving channel 84 since the longitudinal channel edge lips 100 prevent this motion. Toward the syringe distal end 40 the pawl 80 encounters one or more of annular locking elements (locking teeth 108). The pawl 80 rides over the distally pointing tooth or teeth 108 and locks into an irreversible position by wedging the pawl 80 behind a tooth 108.

The sheath 44 can not be removed from the syringe body since the sheath ledge stop 76 eventually abuts the annular stop 112. The sheath ledge stop 76 slides over and past each tooth 108 as the pawl 80 snaps over each tooth 108 until the ledge stop 76 and annular stop 112 meet. Additionally, it must be noted that the annular channel edge lip, that is raised slightly above the outer body surface 24, prevents the pawl 80 from reentering the annular channel 88. Also, remembering that each longitudinal channel edge lip protrudes slightly above not only the outer surface 24 but slightly past the point of a tooth 108. (In this case, "slightly" indicates a distance above the tip of a tooth 108, but less than a distance that would cause a lip (100 or 104) to interfere with the longitudinal movement of a sheath ledge stop 76.) Therefore, since the pawl 80 always rests below the edge lips (100 or 104) and the pawl 80 does not flex from side to side, but only up and down, relative to the inner sheath surface 52, the sheath 44 may not be removed by rotation or twisting.

Figure 5:
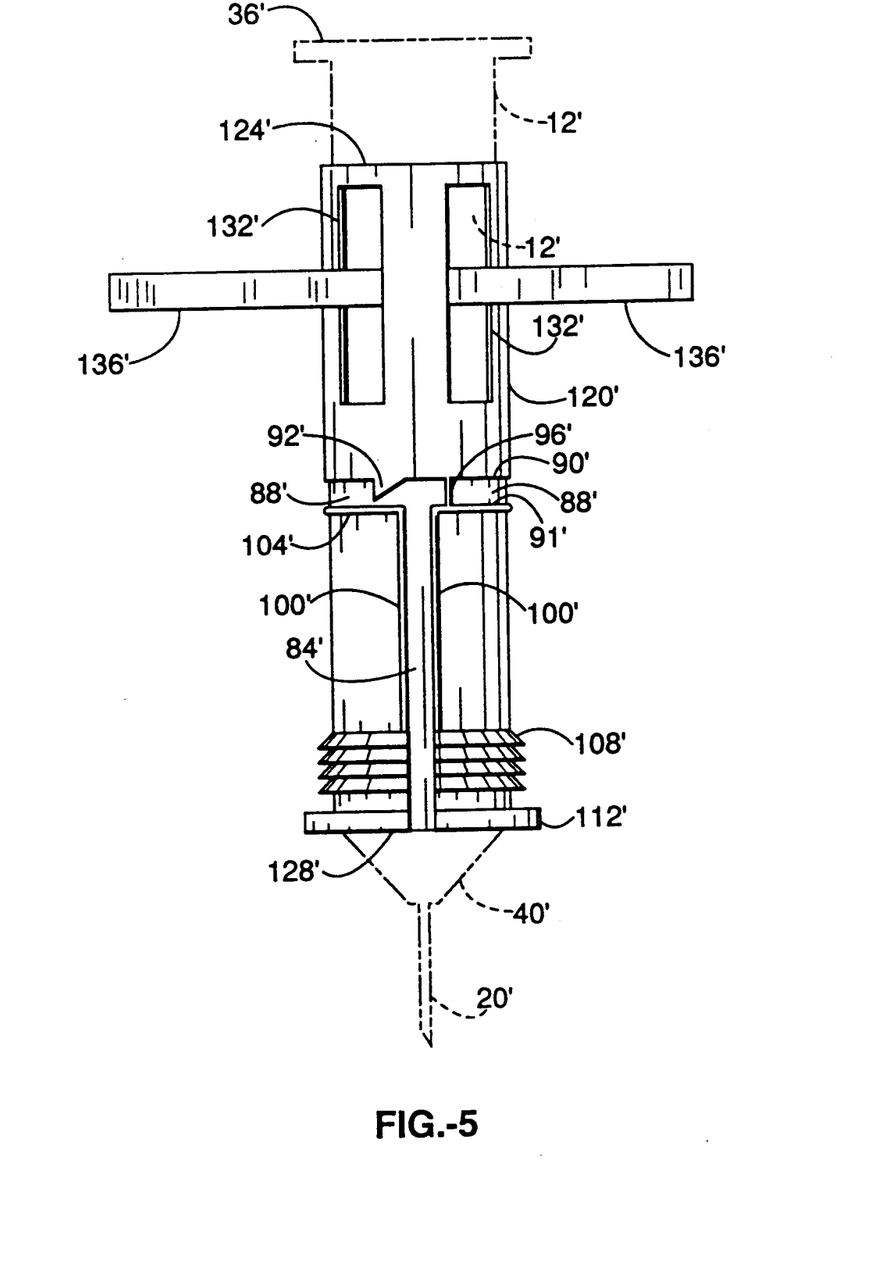
FIG. 5 is an additional embodiment of the subject device comprising a retrofit collar.

An additional embodiment of the subject invention extends the usability of the device to syringes that were not originally manufactured to be fitted with a protective sheath. FIG. 5 illustrates a retrofit collar 120' (primes are used for all equivalent elements to the above disclosed directly molded syringe body components). The collar 120' has proximal 124' and distal ends 128'. Collar 120' slips over a generally smooth syringe until the collar distal end 124' is proximate the distal or needle mounting end 40' of the syringe. Obviously, retrofit collars 120' would be manufactured in various diameter sizes and lengths to accommodate different sized syringes. Once positioned around the syringe, an attachment means, positioned between the collar proximal end 124' and the annular stopping channel 88', securely fastens and holds the collar 120' to the surrounded syringe body 12'. Preferably, the attachment means comprises at least one, and preferably two, and often more, longitudinal slits 132' located and running between the collar proximal end 124' and the annular stopping channel 88' and an adhesive strip 136' for contacting both the collar 120' and the outer syringe body surface 12' through one or more slits 132'. Except for the region of the collar 120' that contains the attachment means, the collar 120' and the earlier described subject device operate the same and contain equivalent components. Naturally, a sheath 44' employed with a collar 120' would need to have an appropriately matched sheath central bore 56'.

Although the retrofit collar 120' is preferably constructed from a plastic like material by standard fabrication procedures, other structurally suitable materials (metals, wood, paper, rubber, and the like) are contemplated to be well within the realm of this disclosure.

The invention has now been explained with reference to specific embodiments. Other embodiments will be suggested to those of ordinary skill in the appropriate art upon review of the present specification.

Although the foregoing invention has been described in some detail by way of illustration and example for purposes of clarity of understanding, it will be obvious that certain changes and modifications may be practiced within the scope of the appended claims.

What is claimed is:

1. An irreversible locking protective syringe device for use on a syringe for sheathing a syringe attached needle post-use, comprising:
    a) a cylindrical syringe body with an outer surface and an inner surface wherein said inner surface surrounds a body longitudinal central cavity entering said body at a proximal end and exiting said body at a restricted needle mounting distal end;
    b) a cylindrical sheath with an outer surface and an inner surface wherein said inner surface surrounds a sheath longitudinal central bore running between proximal and distal sheath ends wherein said sheath central bore has a diameter suitable for receiving and encircling said syringe body;
    c) first means associated with said body for locking said sheath substantially around said body in a pre-use, retracted position wherein said first means includes an annular stopping channel with proximal and distal walls having at least one locking ramp projecting from said proximal wall toward said body distal end substantially narrowing said stopping channel;
    d) second means associated with said body for locking said sheath in an extended position that covers both a portion of said body proximate said distal end and all of said needle in a protective post-use position wherein said second means includes at least one annular element protruding above said outer body surface and at least one stop element protruding above both said outer body surface and said annular element and displaced from said annular element toward said distal body end; and
    e) means associated with said sheath proximal end protruding inwardly from said sheath inner surface for locking said sheath in both pre-use and post-use positions.

2. A protective syringe device according to claim 1, wherein said first means further comprises at least one longitudinal receiving channel with interior wall surfaces and first and second ends for receiving said inwardly protruding sheath locking means where said first channel end is proximate said body distal end and said second channel end intersects said annular stopping channel.

3. A protective syringe device according to claim 1, wherein said annular stopping channel further comprises a channel block for preventing said inwardly protruding sheath locking means from exiting said stopping channel through said longitudinal receiving channel.

4. A protective syringe device according to claim 2, wherein said longitudinal receiving channel has a longitudinal channel edge lip extending along each longitudinal wall edge length on both sides of said receiving channel and protruding above said outer body surface.

5. A protective syringe device according to claim 2, wherein said annular stopping channel has an annular stopping channel edge lip extending along the edge length of said distal wall and protruding above said outer body surface.

6. A protective syringe device according to claim 1, wherein said annular element of said second sheath locking means that protrudes above said outer body surface comprises an annular tooth wherein said tooth is angled toward said body distal end.

7. A protective syringe device according to claim 1, wherein said sheath associated locking means comprises at least one inwardly projecting ledge stop inset within said sheath central bore having a flexible locking pawl secured proximate said ledge stop and projecting at an inward angle towards said sheath proximal end.

8. An irreversible locking protective syringe device for use on a syringe for sheathing a syringe attached needle post-use, comprising:
    a) a cylindrical syringe body with an outer surface and an inner surface wherein said inner surface surrounds a body longitudinal central cavity entering said body at a proximal end and exiting said body at a restricted needle mounting distal end;
    b) a cylindrical sheath with an outer surface and an inner surface wherein said inner surface surrounds a sheath longitudinal central bore running between proximal and distal sheath ends wherein said sheath central bore has a diameter suitable for receiving and encircling said syringe body;

c) first means associated with said body for locking said sheath substantially around said body in a pre-use, retracted position wherein said first means comprises an annular stopping channel with proximal and distal walls with an annular stopping channel edge lip extending along the edge length of said distal wall and protruding above said outer body surface and having within said stopping channel at least one locking ramp projecting from said proximal wall toward said body distal end substantially narrowing said stopping channel and at least one longitudinal receiving channel with interior wall surfaces and first and second ends wherein said first channel end is proximate said body distal end and said second channel end intersects said annular stopping channel wherein said longitudinal receiving channel has a longitudinal channel edge lip extending along each longitudinal wall edge length on both sides of said receiving channel and protruding above said outer body surface;

d) second means associated with said body for locking said sheath in an extended position that covers both a portion of said body proximate said distal end and all of said needle in a protective post-use position wherein said second means includes at least one annular element comprising an annular tooth protruding above said outer body surface and angled toward said body distal end and at least one stop element protruding above both said outer body surface and said annular element and displaced from said annular element toward said distal body end; and e) means associated with said sheath proximal end protruding inwardly from said sheath inner surface for locking said sheath in both pre-use and post-use positions comprising at least one inwardly projecting ledge stop inset within said sheath central bore having a flexible locking pawl secured proximate said ledge stop and projecting at an inward angle towards said sheath proximal end wherein said pawl is sized to fit within said receiving and stopping channels.

9. A protective syringe device according to claim 8, wherein said annular stopping channel further comprises a channel block for preventing said inwardly protruding sheath locking means from exiting said stopping channel through said longitudinal receiving channel.

10. A post-use needle protection safety device for retrofitting a non-protected syringe having a cylindrical syringe body with an outer surface and an inner surface wherein said inner surface surrounds a body longitudinal central cavity entering said body at a proximal end and exiting said body at a restricted needle mounting distal end, comprising;

a) a cylindrical sheath with an outer surface and an inner surface wherein said inner surface surrounds a sheath longitudinal central bore running between proximal and distal sheath ends wherein said sheath comprises means associated with said sheath proximal end protruding inwardly from said sheath inner surface for locking said sheath in both pre-use and needle protective post-use positions and b) a retrofit hollow cylindrical collar with proximal and distal ends and inner and outer surfaces for fitting over said syringe outer body surface, comprising;

first means associated with said collar for locking said sheath substantially around said collar and said syringe body in a pre-use, retracted position wherein said first means includes an annular stopping channel with proximal and distal walls having at least one locking ramp projecting from said proximal wall toward said collar distal end substantially narrowing said stopping channel;

second means associated with said collar positioned distally on said collar from said first means for locking said sheath in an extended position that covers both a portion of said collar proximate said collar and syringe body distal ends and all of said needle in a protective post-use position wherein said second means includes at least one annular element protruding above said collar outer surface and at least one stop element protruding above both said outer collar surface and said annular element and displaced from said annular element toward said distal collar end; and attachment means positioned between said collar proximal end and said first means for securely fastening said retrofit collar around said syringe outer body surface.

11. A retrofit safety device according to claim 10, wherein said attachment means comprises at least one longitudinal slit in said collar located between said proximal collar end and said first means and an adhesive strip for contacting both said collar outer surface and said syringe body outer surface through said longitudinal slit.

12. A retrofit safety device according to claim 10, wherein said first means further comprises at least one longitudinal receiving channel with interior wall surfaces and first and second ends for receiving said inwardly protruding sheath locking means where said first channel end is proximate said collar distal end and said second channel end intersects said annular stopping channel.

13. A retrofit safety device according to claim 10, wherein said annular stopping channel further comprises a channel block for preventing said inwardly protruding sheath locking means from exiting said stopping channel through said longitudinal receiving channel.

14. A retrofit safety device according to claim 12, wherein said longitudinal receiving channel has a longitudinal channel edge lip extending along each longitudinal wall edge length on both sides of said receiving channel and protruding above said outer collar surface.

15. A retrofit safety device according to claim 10, wherein said annular stopping channel has an annular stopping channel edge lip extending along the edge length of said distal wall and protruding above said outer collar surface.

16. A retrofit safety device according to claim 10, wherein said annular element of said second sheath locking means that protrudes above said outer collar surface comprises an annular tooth wherein said tooth is angled toward said collar distal end.

17. A retrofit safety device according to claim 10, wherein said sheath associated locking means comprises at least one inwardly projecting ledge stop inset within said sheath central bore having a flexible locking pawl secured proximate said ledge stop and projecting at an inward angle towards said sheath proximal end wherein said pawl is sized to fit within said receiving and stopping channels.

* * * * *